United States Patent
Kimata et al.

(10) Patent No.: US 6,420,129 B1
(45) Date of Patent: Jul. 16, 2002

(54) REAGENT COMPOSITION FOR DETERMINATION OF ELECTROLYTES

(75) Inventors: Shinsuke Kimata, Tsuruga; Shigeki Asano, Tokyo-to; Yoshihisa Kawamura, Tsuruga, all of (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/424,809

(22) PCT Filed: Mar. 11, 1999

(86) PCT No.: PCT/JP99/01209
§ 371 (c)(1),
(2), (4) Date: Nov. 29, 1999

(87) PCT Pub. No.: WO99/50444
PCT Pub. Date: Oct. 7, 1999

(30) Foreign Application Priority Data

Mar. 31, 1998 (JP) .......................................... 10-086074

(51) Int. Cl.⁷ .......................... C12Q 1/40; A61K 38/43; A61K 31/724
(52) U.S. Cl. ........................... 435/22; 435/201; 514/2; 514/58; 536/103
(58) Field of Search .................... 435/22, 201; 536/103; 514/2, 58

(56) References Cited

U.S. PATENT DOCUMENTS

| 4,709,020 A | 11/1987 | Rauscher et al. ........... 536/17.8 |
| 4,818,692 A | 4/1989 | Rauscher et al. ............. 435/18 |
| 4,987,067 A | 1/1991 | Ishimaru et al. ............... 435/22 |
| 5,378,831 A | 1/1995 | Usui et al. ................ 536/123.1 |
| 5,393,660 A | 2/1995 | Kitahata et al. ............... 435/22 |
| 5,470,715 A | 11/1995 | Mizuguchi et al. ........... 435/22 |

FOREIGN PATENT DOCUMENTS

| GB | 2 081 295 | 2/1982 |
| JP | 51-26284 | 3/1976 |
| JP | 57-29286 | 2/1982 |
| JP | 59-104556 | 6/1984 |
| JP | 60-237998 | 11/1985 |
| JP | 63-17690 | 1/1988 |
| JP | 1-104173 | 4/1989 |
| JP | 1-117786 | 5/1989 |
| JP | 6-113894 | 4/1994 |
| JP | 6-87798 | 11/1994 |
| JP | 2-681635 | 8/1997 |

OTHER PUBLICATIONS

"Rinsho–byorui (clinical pathology)", vol. 37, No. 10, pp. 1155–1159 (1990). Araki et al. Abstract only in English.
"The Enzyme", 3rd ed., vol. 5, pp. 235–271 (1971). Tagaki et al.
"The Journal of Biological Chemistry", vol. 244, pp. 48–54 (Jan. 1969). Pfueller et al.
"Biochemical Society Transactions", vol. 18, pp. 310–311 (1990), Bralin–Kelly et al.

Primary Examiner—James O. Wilson
Assistant Examiner—Leigh C. Maier
(74) Attorney, Agent, or Firm—Kenyon & Kenyon

(57) ABSTRACT

There is provided a reagent composition for the enzymatic determination of electrolytes, which has high solution stability enabling it to stand up to its distribution in the market as a liquid reagent, and which further has excellent quantitative reliability and accuracy. This is a reagent composition for the determination of electrolytes such as calcium or chloride ions, which contains: (a) inactive α-amylase; (b) a chelating agent; (c) a substrate for α-amylase; and (d) a cyclodextrin derivative, and which may optionally further contain an SH group containing compound or a salt thereof.

2 Claims, 4 Drawing Sheets

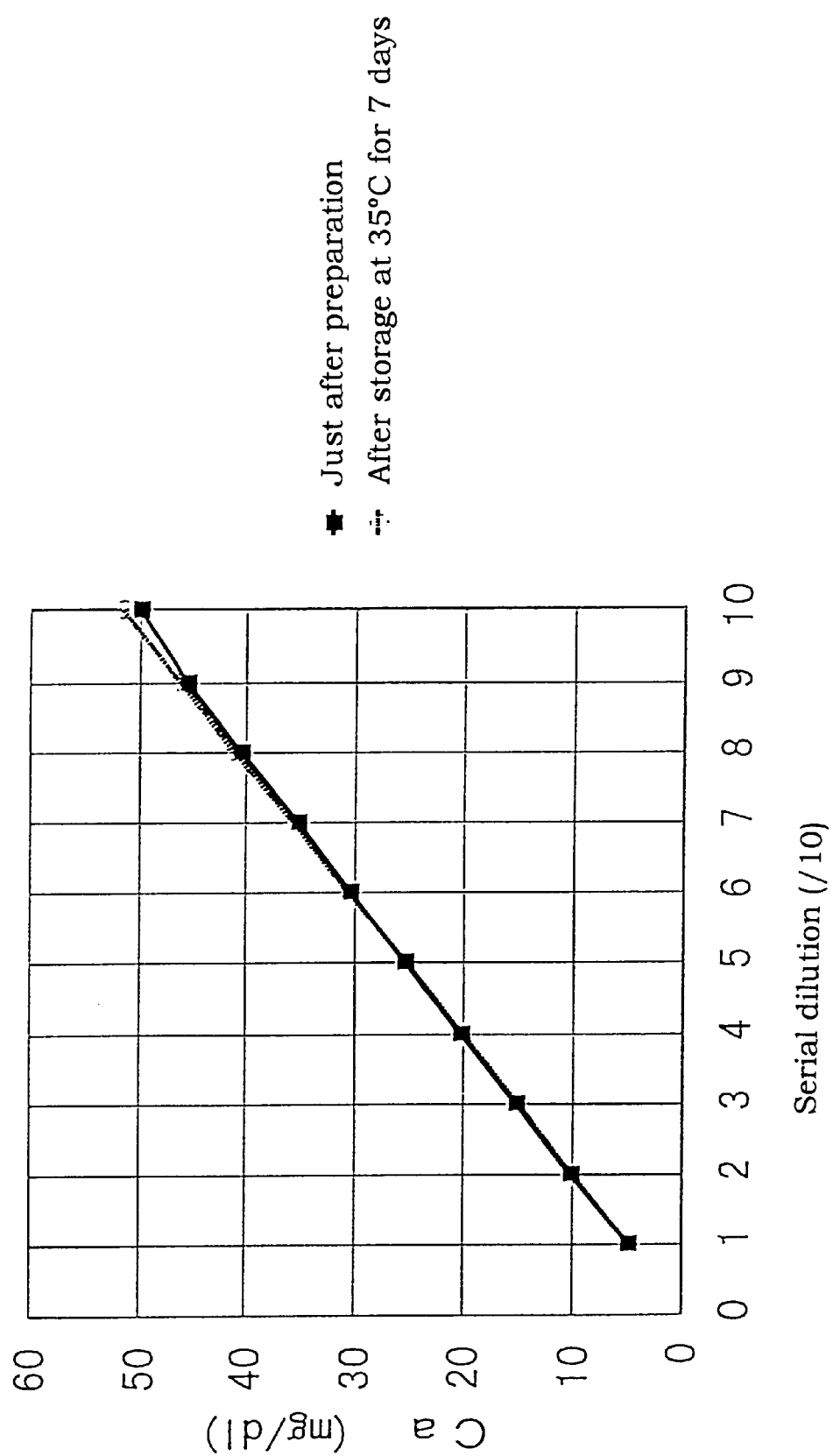

REAGENT COMPOSITION FOR DETERMINATION OF ELECTROLYTES

TECHNICAL FIELD

The present invention relates to a reagent composition for the determination of electrolytes in body fluid, particularly blood or urine, for example, electrolytes such as calcium or chloride ions. More particularly, it relates to a reagent composition for the determination of electrolytes by making use of α-amylase activity.

BACKGROUND ART

In general, the concentrations of electrolytes in a living body, such as calcium and chloride ions, are strictly controlled by metabolism. Therefore, the determination of electrolytes in body fluid is the most standard analysis in the clinical examination on biochemistry, as the barometer of living body functions, and the diagnosis of various diseases is carried out by their determination. For example, the determination of the amount of calcium ions in sera is used for the diagnosis of hypocalcemic diseases such as hypoproteinemia, hypophosphatemia, nephritis, nephrosis, vitamin D deficiency, hypoparathyroidism, and rachitis; or for the diagnosis of hypercalcemic diseases such as bone tumors, Addison's disease, pulmonary emphysema, hyperparathyroidism, and renal insufficiency. The determination of the amount of chloride ions in sera is used for the diagnosis of hypochloremic diseases such as hypotonic dehydration, hyperglucocorticoidosis, and respiratory acidosis; or for the diagnosis of hyperchloremic diseases such as hypertonic dehydration, tubular acidosis, and respiratory alkalosis.

The determination of electrolytes by making use of α-amylase activity is based on the following principles. In the case of calcium ions, inactive α-amylase is activated by calcium ions to decompose a saccharide substrate; and the determination of calcium ions in body fluid is achieved by the determination of a decomposition product (e.g., JP-B 6-87798). In the case of chloride ions, inactive α-amylase is activated by chloride ions as well to decompose a saccharide substrate; and the determination of chloride ions in body fluid is achieved by the determination of a decomposition product (JP-A 3-176000 and JP-A 4-94698).

In these methods, α-amylase is usually used in inactive form by the previous elimination of calcium or chloride ions necessary for the expression of its activity. In these methods, reagents for determination further contain a chelating agent for the purpose of avoiding blank reactions, controlling quantitative reliability by its use as a competitive inhibitor, or masking similar contaminated ions besides the target. The inactive α-amylase is, however, unstable in the presence of a chelating agent, which causes serious problems that the reagents cannot be stored as solutions for a long period of time and there occurs a fluctuation in the values determined.

As the means of making α-amylase stable, there have been known so far, for example, those involving the addition of: calcium ions, chloride ions, or albumin ("Rinsho-byouri (clinical pathology)", vol. 37, no. 10, p. 1155 (1990)); amino acids (JP-A 51-26284); alkali metal salts of acids (JP-A 57-29286); methionine (JP-A 63-17690); aluminum salts (JP-A 1-104173); urea ("The Enzyme", 3rd ed., vol. 5, pp. 235–271 (1971)); guanidine hydrochloride (J. Biol. Chem., vol. 244, pp. 48–54 (1969)); and dithiothreitol or mercaptoethanol (Biochem. Soc. Trans., vol. 18, pp. 310–311 (1990)). These means are, however, insufficient for making inactive α-amylase stable, and particularly in the determination of electrolytes in the presence of a chelating agent, α-amylase begins to be remarkably deactivated just after the preparation of a reagent, which causes a decrease in sensitivity with the lapse of time, resulting in an unfavorable influence upon the values determined; therefore, these means are not suitable for practical use.

In the meantime it is well known that α-cyclodextrin, β-cyclodextrin, or γ-cyclodextrin is useful as a stabilizing agent for proteinase or glycosidase (JP-A 59-104556 and JP-A 1-117786). It is also well known that oligosaccharides such as maltose and α-cyclodextrin, or mixtures thereof, are used as stabilizing agents for inactive α-amylase (JP-A 6-113894). By this means, reagents for determination can stand up to low temperature (2–8° C.) storage for a short period of time (1–2 months); however, it still cannot be said that they have satisfactory stability during long-term storage or at room temperature (18–37° C.) in practical use.

Furthermore, oligosaccharides consisting of 1 to 3 monosaccharides connected in sequence, such as maltose, are products formed from substrates by α-amylase; therefore, from the viewpoint of the principle of determination, they have an unfavorable influence upon the sensitivity and quantitative reliability, which places restrictions on their amounts for use and leads to the drawback that, when they are used as stabilizing agents, other kinds of performance will become worse instead of better. On the other hand, oligosaccharides such as α-cyclodextrin, β--cyclodextrin, and γ-cyclodextrin have the drawbacks that their solubility at low temperatures is poor; they cause the deposition of crystals or the occurrence of white turbidity during storage; and they are not suitable for long-term storage.

For these reasons, the present state of methods for the determination of electrolytes by making use of inactive α-amylase is that high solution stability enabling reagents for determination to stand up to their distribution in the market as liquid reagents presently becoming the main type of reagents for clinical examination has not yet been obtained.

Under these circumstances, an objective of the present invention is to provide a composition for enzymatic determination of electrolytes, which has excellent stability, quantitative reliability, and accuracy.

DISCLOSURE OF THE INVENTION

The present inventors have intensively studied to attain the above objective. They have found that the use of a cyclodextrin derivative as a stabilizing agent for inactive α-amylase results in excellent solution stability during long-term storage from low temperatures to room temperature that is at the level for practical use without any unfavorable influence upon the reaction of α-amylase, and they have further found that the stability as the above objective can be obtained even in low concentrations of a cyclodextrin derivative by the combined use of an SH group containing compound, thereby completing the present invention.

A system for the determination with α-amylase has been well known, in which glucosyl-α-cyclodextrin and/or maltosyl-α-cyclodextrin are used as easily soluble clathrate compounds for p-nitrophenyl succharide substrates and the detection is carried out for nitrophenol liberated by the action of α-amylase activity (JP-B 2681635). In this system, the α-amylase is in active form and no chelating compound is used. Therefore, it does not suggest the stability of inactive α-amylase in the reagent composition of the present invention as a liquid reagent in the presence of a chelating compound.

Thus, the present invention provides a reagent composition for the determination of electrolytes, characterized in that it comprises: (a) inactive α-amylase; (b) a chelating agent; (c) a substrate for α-amylase; and (d) a cyclodextrin derivative.

The present invention further provides a reagent composition for the determination of electrolytes, which comprises: (a) inactive α-amylase; (b) a chelating agent; (c) a substrate for α-amylase; and (d) a cyclodextrin derivative, and which may optionally further comprise (e) an SH group containing compound or a salt thereof.

The reagent composition for the determination of electrolytes according to the present invention achieves the determination of electrolytes in a sample by utilizing the fact that inactive α-amylase is activated by ions such as calcium or chloride ions, which are activating agents for α-amylase, and by the determination of a decomposition product formed by the action of the active α-amylase. It follows the principle of determination as described below.

(1) In the case of a method in which a maltooligosaccharide is used as a substrate, for example, maltotetraose, maltopentaose, or maltohexaose is used as the substrate, from which glucose is liberated by the action of activated α-amylase and by the supplementary action of a following enzyme such as α-glycosidase, and the amount of glucose is determined to know the amount of electrolytes such as calcium.

The method for the determination of glucose produced may include glucose oxidase-peroxidase method and hexokinase-glucose-6-phosphate dehydrogenase method.

In the glucose oxidase-peroxidase method, glucose oxidase is allowed to act on the glucose liberated to form hydrogen peroxide, which is oxidatively condensed with an oxidative coloring substance, such as phenol, and a coupler in the presence of peroxidase to form a quinone dye, of which absorbance is measured by the rate assay.

In the hexokinase-glucose-6-phosphate dehydrogenase method, the glucose liberated is converted into glucose-6-phosphate by hexokinase and glucose-6-phosphate dehydrogenase is subsequently allowed to act on the glucose-6-phosphate in the presence of $NAD^+$ or $NADP^+$, at which time the increasing reaction of NADH or NADPH is measured by the rate assay.

(2) In the case of a method in which a maltooligossacharide derivative with a phenyl or naphthyl group, or a derivative thereof, which has been attached as an aglycon to the reducing end thereof, is used as a substrate, for example, p-nitrophenylmaltopentaoside, p-nitrophenylmaltohexaoside, p-nitrophenylmaltoheptaoside, 2,4-dichloronitrophenylmaltopentaoside, 2-chloro-4-nitrophenylmaltotrioside, or 2-chloro-4-nitrophenylmaltopentaoside is used as the substrate, from which the aglycon is liberated by the action of activated α-amylase and, if necessary, by the supplementary action of a following enzyme such as α-glucosidase, and the amount of aglycon liberated is optically determined to know the amount of electrolytes such as calcium.

(3) In the case of a method in which a maltooligosaccharide derivative with a phenyl or naphthyl group, or a derivative thereof, which has been attached as an aglycon to the reducing end thereof, and further with a 4- or 6-hydroxy group of the glucose at the non-reducing end thereof, which has been modified by any means, is used as a substrate, this method follows the procedures as described above in (2) and may include those using a substrate of the following type: the glucose at the non-reducing end thereof has been modified, for example, by halogen or a glucopyranosyl group (e.g., JP-A 60-237998); the 4- or 6-hydroxy group has been replaced by an alkyl, alkoxy, or phenyl group (e.g., JP-A 60-54395, JP-A 1-157996); or the 4- or 6-hydroxy group has been replaced by a β-galactopyranosyl group (e.g., JP-A 3-264596, JP-A 6-315399).

Among these well-known methods of determination, the method of determination as described above in (3) is excellent from the viewpoint of its principle; in particular, the method using 2-chloro-4-nitrophenyl-4-O-β-D-galactopyranosyl-α-maltoside has the merits that the modification of its non-reducing end avoids an increase in the reagent blank caused, for example, by the decomposition of endogenous α-glucosidase; no need of following enzymes gives a reduced cost; and high affinity of α-amylase to the substrate leads to high sensitivity. This is therefore particularly preferred as the method for the determination of electrolytes according to the present invention.

As one embodiment of the present invention, the determination of calcium ions is described below. A reagent composition for the determination of electrolytes, which comprises inactive α-amylase, a chelating agent, a substrate for α-amylase, and a cyclodextrin derivative, and which may optionally further comprises an SH group containing compound, is allowed to act on the calcium ions in a sample. For example, 2-chloro-4-nitrophenyl-4-O-β-D-galactopyranosyl-α-maltoside is then allowed to act as an additional substrate for α-amylase, and the amount of 2-chloro-4-nitrophenol liberated is determined to know the amount of calcium in the sample.

The cyclodextrin derivative as used in the present invention is what is called a branched-chain cyclodextrin derivative and such a derivative may include glucosyl-α-cyclodextrin, maltosyl-α-cyclodextrin, glucosyl-β-cyclodextrin, maltosyl-β-cyclodextrin, glucosyl-γ-cyclodextrin, maltosyl-γ-cyclodextrin, methyl-β-cyclodextrin, carboxymethyl-β-cyclodextrin, triacetyl-β-cyclodextrin, hydroxyethyl-β-cyclodextrin, and hydroxypropyl-β-cyclodextrin. These compounds usually have side chains introduced for the improvement of water solubility. These side chains may be introduced in any number into the ring structure of cyclodextrin for the purpose of improving the solubility. These derivatives may be used in combination.

The concentration of a cyclodextrin derivative as used in the reagent composition is in the range of 0.01 to 100 mM. Taking into consideration the unfavorable influence of impurities or other substances contained in the cyclodextrin derivative upon the reaction of α-amylase and the unfavorable influence of the clathration of a coloring group such as nitrophenol in the cyclodextrin upon the sensitivity, the concentration is preferably in the. range of 1 to 12 mM.

The SH group containing compound as used in the present invention refers to those having protective or anti-oxidative action to the SH groups of proteins or other substances, or those having reductive and cleaving action to the disulfide linkages of proteins or other substances. Examples of the SH group containing compound are N-acetylcysteine, dithiothreitol, glutathione, thioglycerol, mercaptoethanol, thiosalicylic acid, and thiourea. In particular, N-acetylcysteine and reduced glutathione are preferred. The concentration of an SH group containing compound as used in the reagent composition is in the range of 0.01 to 50 mM. Taking into consideration the solubility or other factors, the concentration is preferably in the range of 0.01 to 20 mM. These SH group containing compounds may be used in combination.

The α-amylase as used in the present invention may be derived from any source of microorganisms, plants, or animals, preferably from an animal source, for example, α-amylase derived from the swine pancreas. However, the α-amylase as used in the present invention should be inactive by demineralization. As described above, inactive α-amylase is converted into active α-amylase by getting electrolytes such as calcium or chloride ions in a sample and the active α-amylase reacts with a substrate for α-amylase. The technique of demineralization may include dialysis, ultrafiltration, ion exchange, and elimination with a column. The concentration of inactive α-amylase as used in the reagent composition is preferably in the range of 0.5 to 1000 IU/ml.

The chelating agent as used in the present invention may include ethylenediaminetetraacetic acid and salts thereof, glycoletherdiaminetetraacetic acid, 1,2-bis(o-aminophenoxy)ethanetetraacetic acid, and trans-1,2-diaminocyclohexanetetraacetic acid. The role of a chelating agent in the composition for the determination of electrolytes may include, as described above, the avoidance of blank reactions, the control of quantitative reliability by its use as a competitive inhibitor, or the masking of similar contaminated ions besides the target. On the contrary, the use of a chelating agent may also be one of the factors causing the deactivation of α-amylase. Therefore, the concentration of a chelating agent as used in the reagent composition is preferably in the range of 0.01 to 10 mM, although the concentration should be determined, taking into consideration the above reasons. These chelating agents may be used in combination.

As described above, the substrate for α-amylase involved in the present invention is not particularly limited; however, 2-chloro-4-nitrophenylmaltotrioside and 2-chloro-4-nitrophenyl-4-O-β-D-galactopyranosylmaltoside are preferred from the viewpoint of the merit that no need of following enzymes gives a reduced cost, while 2-chloro-4-nitrophenyl-4-O-β-D-galactopyranosylmaltoside is preferably used from the viewpoint of the merits that the modification of its non-reducing end avoids an increase in the reagent blank caused, for example, by the decomposition of endogenous α-glucosidase and high affinity of α-amylase to the substrate leads to high sensitivity. The concentration of a substrate of α-amylase as used in the reagent composition is preferably in the range of 0.1 to 50 mM.

In the reagent composition of the present invention, two substrates requiring different methods of optical measurement at the final stage may be used in combination, if necessary, for the purpose of reducing reagent blanks and improving quantitative reliability, whereby a competition is caused between the glycolysis reactions and the apparent affinity to the substrates can be reduced. For example, one substrate selected from maltooligosaccharides or their derivatives with a non-coloring group attached to the glucose at the reducing end thereof is allowed to compete, thereby controlling the rate of the reaction of α-amylase to another substrate with a coloring group attached to the glucose at the reducing end thereof and an optional substituent group attached to the non-reducing end thereof, which is the main reaction.

The maltooligosaccharide as used herein may include, for example, maltooligosaccharides having the glucose number of 2 to 7, such as maltose, maltopentaose, maltohexaose, and maltoheptaose. The maltooligosaccharide with a non-coloring group attached to the glucose at the reducing end thereof may include, for example, 2,4-dichlorophenyl-α-D-maltotrioside, 2,4-dichlorophenyl-(α or β)-D-maltopentaoside, and 2,4-dichlorophenyl-(α or β)-D-maltotrioside. The concentration of a maltooligosaccharide as used in the reagent composition is preferably in the range of 50 to 250 mM.

The reagent composition of the present invention has the final pH ranging from 5.0 to 8.0, making it possible to control the rate of the glycolysis reaction of α-amylase itself still better and to thereby extend the limits of determination. In contrast, α-amylase has the optimum pH 6 to 8 around the neutral point for stability, and it is therefore considered that the reagent composition of the present invention is preferably prepared in the pH range of 6 to 8. To obtain quantitative reliability and other kinds of performance at the same time, the reagent composition of the present invention may be formulated by the incorporation of an additional reagent for controlling the final pH and the division of the reagents into the first ones and the second ones so that the optimum pH for the reaction can be achieved by the mixing of these reagents. The means of keeping the reagent pH is not particularly limited, so long as it is well known; in general, it involves the use of a buffer. The buffer to be used may include, for example, Good's buffers, tris buffers, and phosphate buffers. The buffer is preferably used in a concentration of 10 to 500 mM.

The means of obtaining quantitative reliability in a state keeping the stability of reagents, which is to be attained by the present invention, may include, as described above: (1) the addition of a chelating agent; (2) the addition of a maltooligosaccharide; and (3) the control of a reagent pH. These means can be used alone or in combination.

To avoid any unfavorable influence of interfering electrolytes or to make a control of sensitivity, the reagent composition of the present invention may optionally further comprise, if necessary, selective binders for the interfering electrolytes or target electrolytes, such as ionophores and crown ethers. The selective binder may include, in addition to the above chelating agents, 18-crown-6 (Merck & Co., In.) and Kryptofix 221 (Merck & Co. Inc.). If necessary, preservatives, surfactants, antioxidants, protease inhibitors, and other additives may also be used to an extent that they have no unfavorable influence upon the quantitative reliability for electrolytes to be determined.

The preservatives are not particularly limited; for example, sodium azide or antibiotics such as cefems, penicillins, aminoglycosides, and quinolones, which have little influence upon the stability of α-amylase, are preferably used. These preservatives can be used alone or in combination. As the surfactants, for example, those of the non-ionic, cationic, or anionic type can be used alone or in combination.

When the electrolytes to be determined are calcium ions, it is preferred to add alkali metal halides such as sodium chloride or potassium chloride in concentrations of 3 to 300 mM. When the electrolytes to be determined are chloride ions, divalent cations such as calcium, magnesium, barium, or zinc ions can be added in concentrations of 0.01 to 200 mM.

The antioxidants may include ascorbic acid and salts thereof, saccharides such as sorbose, and catalase. The protease inhibitors may include PMSF.

The present invention utilizes the fact that inactive α-amylase is converted into active α-amylase, as described above, by getting electrolytes such as calcium or chloride ions in a sample and the active α-amylase reacts with a substrate for α-amylase. According to the procedures based on the above methods of determination that themselves are well known, the determination can be carried out. For example, in the determination of calcium, a reagent composition for the determination of electrolytes, which comprises inactive α-amylase, a chelating agent, and a cyclodextrin derivative, and which may optionally further comprise an SH group containing-compound, is allowed to act on the calcium ions in a sample, and 2-chloro-4-nitrophenyl-4-O-β-D-galactopyranosyl-α-maltoside is then allowed to act as an additional substrate for α-amylase, whereby 2-chloro-4-nitrophenol is produced by the reaction of α-amylase activated depending upon the amount of calcium. Because 2-chloro-4-nitrophenol itself exhibits the absorption of light at about 400 nm, the change of absorbance at about 400 nm is measured after the liberation to determine the concentration of calcium in the sample using the absorbance of a sample with a known concentration as a control. As the method for the determination of 2-chloro-4-nitrophenol, any assay can be used, the rate assay in which the reaction of amylase is continuously monitored, or the end point assay in which the reaction is allowed to proceed for a fixed time and then stopped before determination.

As another embodiment of the present invention, the determination of chloride ions is described below. A reagent composition for the determination of electrolytes, which comprises inactive α-amylase, a chelating agent, a substrate for α-amylase, and a cyclodextrin derivative, and which may optionally further comprise an SH group containing compound, is allowed to act on the chloride. ions in a sample, and 2-chloro-4-nitrophenyl-4-O-β-D-galactopyranosyl-α-maltoside is then allowed to act as an additional substrate for α-amylase, followed by the determination of 2-chloro-4-nitrophenol liberated to know the amount of chloride ions in the sample.

BEST MODE FOR CARRYING OUT THE INVENTION

The present invention will be further illustrated by the following examples; however, the present invention is not limited to these examples.

EXAMPLE 1

Among the reagents for the determination of calcium with the reagent formulations as described below, test enzyme solutions were prepared by the addition of glucosyl-α-cyclodextrin (G1αCD), maltosyl-α-cyclodextrin (G2αCD), glucosyl-p-cyclodextrin (G1βCD), or maltosyl-β-cyclodextrin(G2βCD) as a cyclodextrin derivative to have a concentration of 0, 1.5, 3, 6, or 12 mM. To the test enzyme solutions containing 3 mM glucosyl-β-cyclodextrin was further added independently N-acetylcysteine or reduced glutathione to have a concentration of 2.5, 5, 10, or 20 mM.

| A. Reagent formulations | |
|---|---|
| (1) Test enzyme solutions | |
| Tris hydrochloric acid buffer (pH 7.3) | 50 mM |
| Inactive α-amylase (from swine pancreas) | 1.7 IU/ml |
| NaCl | 200 mM |
| 1,2-Bis(o-aminophenoxy)ethanetetraacetic acid | 0.8 mM |
| Maltose | 160 mM |
| Polyoxyethylene octyl phenyl ether | 0.05% |
| Cyclodextrin derivative | shown in Table 1 |
| SH group containing compound | shown in Table 1 |
| (2) Test substrate solution | |

| A. Reagent formulations | |
|---|---|
| -continued | |
| Good's buffer (pH 5.7) | 300 mM |
| NaCl | 200 mM |
| Maltose | 160 mM |
| Polyoxyethylene octyl phenyl ether | 0.05% |
| 2-Chloro-4-nitrophenyl-4-O-β-D-galactopyranosyl-α-maltoside | 0.8 mM |

Both kinds of test solutions prepared by the above procedures were stored at 4° C. for 3 months. Visual observation of the test solutions was carried out just after the preparation and after the storage to examine whether there was found the deposition of crystals or the presence of white turbidity. The results are shown in table 1 for the visual observation just after the preparation and in Table 2 for the visual observation after the storage.

Comparative Example 1

The test solutions were prepared in the same manner as described in Example 1, except that α-cyclodextrin (αCD) (1.5, 3, 6, or 12 mM), β-cyclodextrin (βCD) (1.5, 3, 6, or 12 mM), or γ-cyclodextrin (γCD) (1.5, 3, 6, or 12 mM) was independently added instead of the cyclodextrin derivatives and the SH group containing compounds in the above reagent formulations to have the respective concentrations as shown in Table 1. Both kinds of test solutions were stored at 4° C. for 3 months. Visual observation of the test solutions was carried out just after the preparation and after the storage to examine whether there was found the deposition of crystals or the presence of white turbidity. The results are shown in Table 1 for the visual observation just after the preparation and in Table 2 for the visual observation after the storage.

TABLE 1

| Ex. | Agent added (concentration in mM) | 0 | 1.5 | 3 | 6 | 12 |
|---|---|---|---|---|---|---|
| | no addition | – | | | | |
| | G1αCD | | – | – | – | – |
| | G1βCD | | – | – | – | – |
| | G2αCD | | – | – | – | – |
| | G2βCD | | – | – | – | – |

| | Agent added (concentration in mM) | 0 | 2.5 | 5 | 10 | 20 |
|---|---|---|---|---|---|---|
| | 3 mM G1βCD + NAC | – | – | – | – | – |
| | 3 mM G1βCD + GSH | – | – | – | – | – |

| Comp. Ex. | Agent added (concentration in mM) | 1.5 | 3 | 6 | 12 |
|---|---|---|---|---|---|
| | αCD | – | – | + | + |
| | βCD | – | – | + | + |
| | γCD | – | – | + | + |

+: turbidity found –: no turbidity
G1: glucosyl
G2: maltosyl
CD: cyclodextrin
NAC: N-acetylcysteine
GSR: reduced glutathione

TABLE 2

| Ex. | Agent added (concentration in mM) | 0 | 1.5 | 3 | 6 | 12 |
|---|---|---|---|---|---|---|
| | no addition | – | | | | |
| | G1αCD | | – | – | – | – |
| | G1βCD | | – | – | – | – |
| | G2αCD | | – | – | – | – |
| | G2βCD | | – | – | – | – |

| | Agent added (concentration in mM) | 0 | 2.5 | 5 | 10 | 20 |
|---|---|---|---|---|---|---|
| | 3 mM G1βCD + NAC | – | – | – | – | – |
| | 3 mM G1βCD + GSH | – | – | – | – | – |

| Comp. Ex. | Agent added (concentration in mM) | 1.5 | 3 | 6 | 12 |
|---|---|---|---|---|---|
| | αCD | – | + | + | + |
| | βCD | – | + | + | + |
| | γCD | – | + | + | + |

As can be seen from Tables 1 and 2, the test enzyme solutions containing α-cyclodextrin, β-cyclodextrin, or γ-cyclodextrin in Comparative Example 1 had already become turbid just after the preparation at 6 mM and became turbid after the storage at 4° C. for 3 months at 3 mM. In contrast, it is found that the test enzyme solutions containing cyclodextrin derivatives in Example 1 had no turbidity and remained clear even at 12 mM that was the highest concentration under the conditions of experiment.

EXAMPLE 2

In the test enzyme solutions of the reagents for the determination of calcium with the reagent formulations as described above in Example 1, glucosyl-α-cyclodextrin, maltosyl-α-cyclodextrin, glucosyl-β-cyclodextrin, or maltosyl-β-cyclodextrin was independently added as a cyclodextrin derivative at 12 mM.

To the test enzyme solutions containing 3 mM glucosyl-β-cyclodextrin was further added independently N-acetylcysteine or reduced glutathione to have a concentration of 20 mM, followed by storage at 35° C. for 7 days. The activity of α-amylase in the test enzyme solutions just after the preparation and after the storage at 35° C. for 7 days was measured with a commercially available reagent for the determination of α-amylase activity (DIACOLOR-LIQUID AMY; manufactured by Toyo Boseki K.K.) to determine the residual activity (%) after the storage at 35° C. for 7 days. The results are shown in Table 3 and FIG. 1.

Comparative Example 2

Instead of the cyclodextrin derivatives and the SH group containing compounds in the reagent formulations as described above in Example 1, glucose (100 mM), maltose (50 mM), maltotriose (30 mM), α-cyclodextrin (1.5 mM), β-cyclodextrin (1.5 mM), γ-cyclodextrin (1.5 mM), N-acetylcysteine (20 mM), or reduced glutathione (20 mM) was independently added to have the respective concentrations as shown in Table 3. The test solutions thus prepared were stored at 4° C. for 3 months or at 35° C for 7 days in the same manner as described in Example 2, and the activity of α-amylase in the test enzyme solutions was measured to determine the residual activity (%) after the storage at 35° C. for 7 days. The results are shown in Table 3 and FIG. 1.

TABLE 3

| No. | Agent added | Residual activity (%) |
|---|---|---|
| 1 | no addition | 67.6 |
| 2 | G1αCD (12 mM) | 80.4 |
| 3 | G1βCD (12 mM) | 91.7 |
| 4 | G2αCD (12 mM) | 82.3 |
| 5 | G2βCD (12 mM) | 93.0 |
| 6 | 3 mM G1βCD + NAC (20 mM) | 94.5 |
| 7 | 3 mM G1βCD + GSH (20 mM) | 95.8 |
| 8 | glucose (100 mM) | 67.4 |
| 9 | maltose (50 mM) | 73.5 |
| 10 | maltotriose (30 mM) | 77.3 |
| 11 | αCD (1.5 mM) | 70.5 |
| 12 | βCD (1.5 mM) | 77.4 |
| 13 | γCD (1.5 mM) | 74.6 |
| 14 | NAC (20 mM) | 71.2 |
| 15 | GSH (20 mM) | 75.4 |

As can be seen from Table 3 and FIG. 1, the stability of α-amylase was improved by the addition of a. cyclodextrin derivative or by the supplementary addition of an SH group containing compound in Example 2, as compared with the case of no addition and Comparative Example 2.

EXAMPLE 3

In the test enzyme solutions of the reagents for the determination of calcium with the reagent formulations as described above in Example 1, glucosyl-α-cyclodextrin, maltosyl-α-cyclodextrin, glucosyl-β-cyclodextrin, or maltosyl-β-cyclodextrin was independently added as a cyclodextrin derivative at 0, 1.5, 3, 6, or 12 mM. To the test enzyme solutions containing 3 mM glucosyl-β-cyclodextrin was further added independently N-acetylcysteine or reduced glutathione at 2.5, 5, 10, or 20 mM, and the determination of calcium ions with a calcium standard solution was carried out as described below.

According to the method as described below, the determination of the amount of calcium was carried out for test solutions just after the preparation with 10 mg/dl calcium standard solution as a sample, and the relative sensitivity (%) was determined under the respective reagent conditions when the sensitivity in the case of no addition of cyclodextrin derivatives was taken as 100%. The results are shown in Table 4.

B. Method for the Determination of the Amount of Calcium

To 5.8 μl of a sample was added 180 μl of a test enzyme solution, and the mixture was pre-warmed for 5 minutes, to which 90 μl of a test substrate solution was further added to make the reaction start. The change of absorbance per minute for 3 minutes was measured starting at the time when 2 minutes passed after the addition of the test substrate solution, and the amount of calcium in the sample was determined according to the two-point calibration curves for purified water and 10 mg/dl calcium standard solution.

The measuring apparatus used was HITACHI Automatic Analyzer model 7170. The measurement wavelength was 405 nm for the principal wavelength and 546 nm for the second wavelength. The measurement was carried out at 37° C.

Comparative Example 3

Instead of the cyclodextrin derivatives and the SH group containing compounds in the reagent formulations as described above in Example 1, maltose (6.3, 12.5, 25, or 50 mM) or maltotriose (3.8, 7.5, 15, or 30 mM) was independently added at the respective concentrations as shown in Table 4. The test solutions thus prepared were used for the determination of the calcium standard solution in the same manner as described in Example 3. The results are shown in Table 4.

TABLE 4

RELATIVE SENSITIVITY (%) WHEN SENSITIVITY
IN CASE OF NO ADDITION IS TAKEN AS 100%

| | Agent added (concentration in mM) | 0 | 1.5 | 3 | 6 | 12 |
|---|---|---|---|---|---|---|
| Ex. | no addition | 100.0 | | | | |
| | G1αCD | | 112.8 | 120.2 | 122.3 | 118.9 |
| | G1βCD | | 120.7 | 128.6 | 133.2 | 122.5 |
| | G2αCD | | 112.5 | 123.0 | 119.4 | 122.8 |
| | G2βCD | | 122.8 | 120.7 | 120.2 | 123.0 |
| | Agent added (concentration in mM) | 0 | 2.5 | 5 | 10 | 20 |
| | 3 mM G1βCD + NAC | 124.3 | 123.0 | 123.8 | 123.3 | 123.5 |
| | 3 mM G1βCD + GSH | | 123.5 | 123.0 | 123.3 | 123.3 |
| Comp. Ex. | Agent added (concentration in mM) | 6.3 | 12.5 | 25 | 50 | |
| | maltose | 99.7 | 89.3 | 83.9 | 70.1 | |
| | Agent added (concentration in mM) | 3.8 | 7.5 | 15 | 30 | |
| | maltotriose | 47.1 | 24.3 | 7.4 | 4.6 | |

As can be seen from Table 4, the sensitivity in the determination of the standard solution was remarkably decreased by the addition of maltose or maltotriose in Comparative Example 3. In contrast, the sensitivity was improved by the addition of a cyclodextrin derivative in Example 3, and there are found almost no fluctuation in the sensitivity at 1.5 mM or higher and no fluctuation in the sensitivity even by the supplementary addition of an SH group containing compound.

EXAMPLE 4

In the test enzyme solutions of the reagents for the determination of calcium with the reagent formulations as described above in Example 1, glucosyl-β-cyclodextrin was added at 12 mM. To the test enzyme solutions containing 3 mM glucosyl-β-cyclodextrin was further added reduced glutathione at 20 mM, followed by storage at 35° C. for 7 days. According to the method for the determination of the amount of calcium as described in Example 3, Sec. B, the calcium linearity was determined for test solutions just after the preparation and after the storage at 35° C. for 7 days with serial 10-fold dilutions of a 50 mg/dl aqueous calcium solution as samples. The results are shown in FIG. 3 and Table 4.

Comparative Example 4

Instead of the cyclodextrin derivatives and the SN-group containing compounds in the reagent formulations as described above in Example 1, β-cyclodextrin was added at 1.5 mM. The test solutions thus prepared were stored at 35° C. for 7 days and the calcium linearity was determined in the same manner as described in Example 3. The results are shown in FIG. 2.

As can be seen from FIG. 2, the linearity after the storage at 35° C. for 7 days when β-cyclodextrin was added in Comparative Example 4 became deviated upward, and the quantitative reliability was decreased at high concentrations. In contrast, it is found that when glucosyl-β-cyclodextrin was added or when reduced glutathione was added together with glucosyl-β-cyclodextrin, the quantitative reliability was kept at high concentrations even after the storage at 35° C. for 7 days.

The reagent composition for the determination of electrolytes according to the present invention can provide the effect of α-amylase stabilization without any unfavorable influence upon the enzymatic reaction of α-amylase, by the addition of a cyclodextrin derivative as a stabilizing agent for inactive α-amylase or by the supplementary addition of an SH group containing compound. The reagent composition further has excellent solution stability during long-term storage from low temperatures to room temperature that is at the level for practical use. This is a composition for the enzymatic determination of electrolytes, which has excellent stability, quantitative reliability, and accuracy.

BRIEF DESCRIPTION OF THE DRAWINGS

FIG. 4: a graph showing the calcium linearity just after the preparation and after the storage at 35° C. for 7 days when 20 mM reduced glutathione was added together with 12 mM glucosyl-β-cyclodextrin in Example 4.

Figure 1:
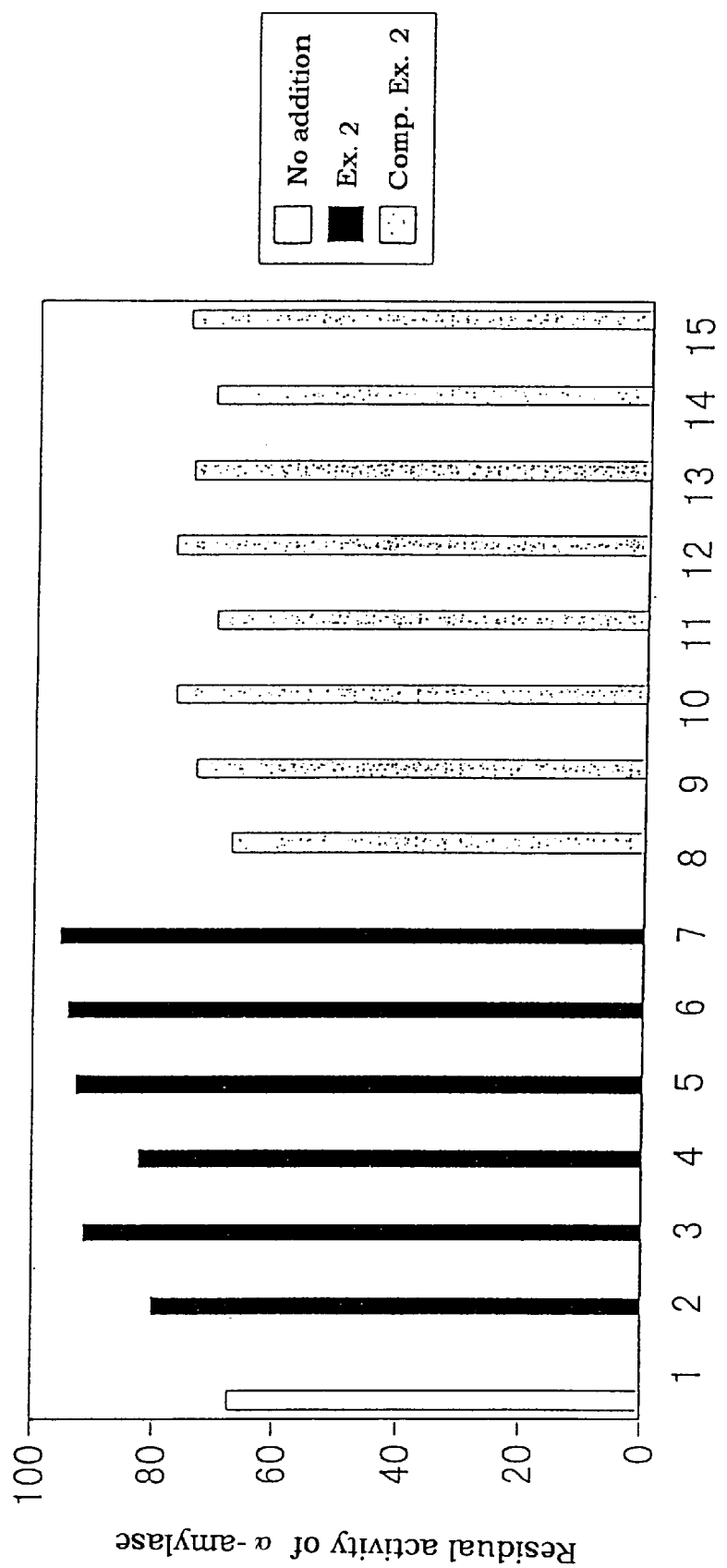
FIG. 1: a graph showing the residual activity of α-amylase after the storage at 35° C. for 7 days in Example 2 and Comparative Example 2. The ordinate and the abscissa indicate the residual activity of α-amylase (%) and the corresponding composition numbers, respectively.
Figure 2:
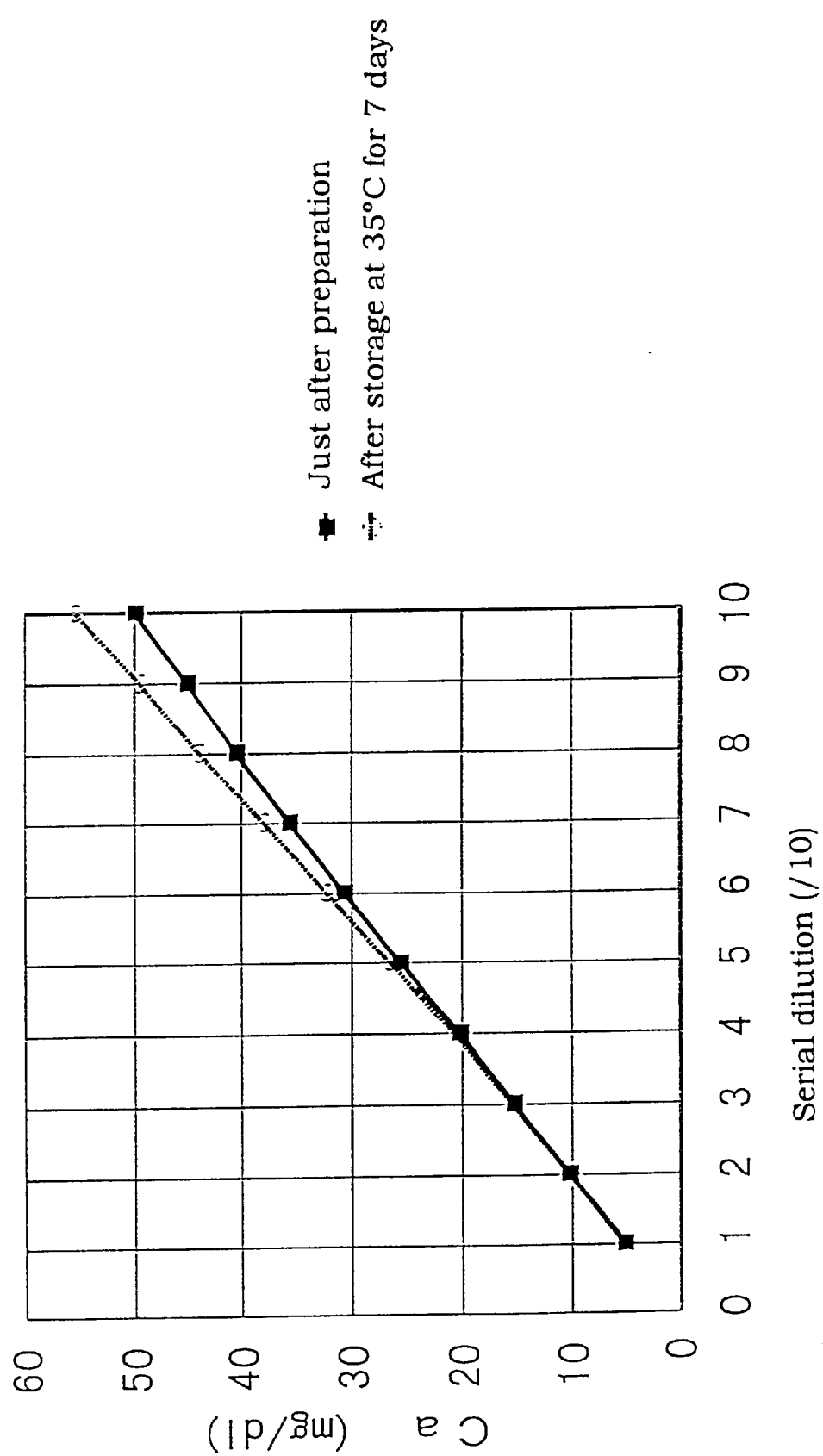
FIG. 2: a graph showing the calcium linearity just after the preparation and after the storage at 35° C. for 7 days when 1.5 mM β-cyclodextrin was added in Comparative Example 4.
Figure 3:
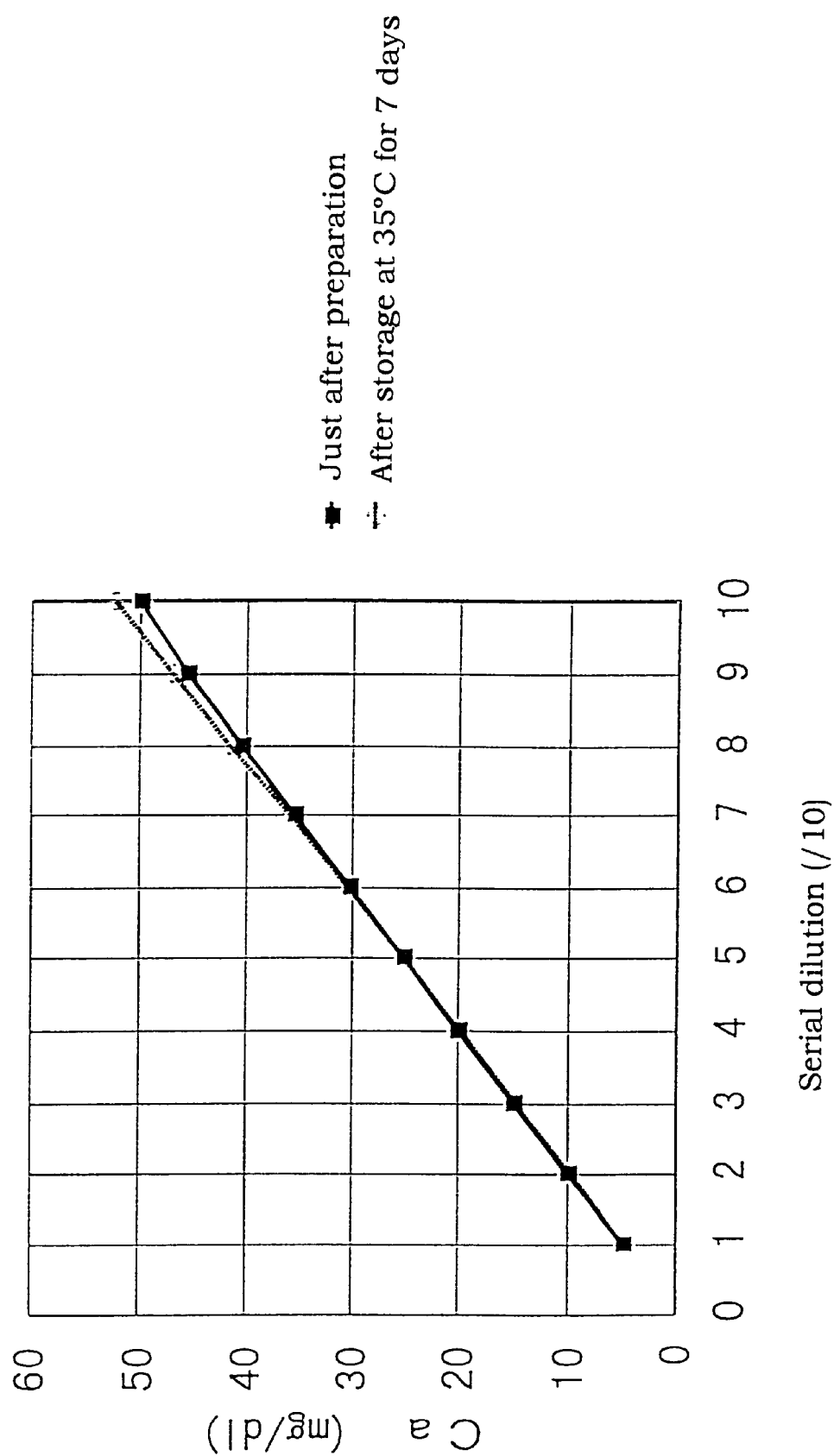
FIG. 3: a graph showing the calcium linearity just after the preparation and after the storage at 35° for 7 days when 12 mM glucosyl-β-cyclodextrin was added in Example 4.

What is claimed is:

1. A reagent composition for the determination of electrolytes, characterized in that it comprises: (a) inactive α-amylase; (b) a chelating agent; (c) a substrate for α-amylase; (d) a cyclodextrin derivative; and (e) an SH group containing compound or salt thereof.

2. The reagent composition for the determination of electrolytes according to claim 1, wherein the SH group containing compound is N-acetyl-cysteine or reduced glutathione.

* * * * *